United States Patent [19]

Cecere et al.

[11] 4,320,132

[45] Mar. 16, 1982

[54] ANTIBOTRYTICAL PYRAZOLO-TRIAZOL-TRIONES

[75] Inventors: Mirella Cecere; Franco Gozzo; Simone Lorusso; Carlo Garavaglia, all of Milan, Italy

[73] Assignee: Montedison S.p.A., Milan, Italy

[21] Appl. No.: 148,387

[22] Filed: May 9, 1980

[30] Foreign Application Priority Data

May 11, 1979 [IT] Italy .................................. 22553 A/79

[51] Int. Cl.³ .................... A01N 43/90; C07D 487/04
[52] U.S. Cl. .................................... 424/269; 548/264; 548/367
[58] Field of Search .......................... 548/264; 424/269

[56] References Cited

U.S. PATENT DOCUMENTS 3,912,735 10/1975 Von Bredow et al. ............. 548/264
4,088,767 5/1978 Shigematsu et al. ................ 548/264
4,249,934 2/1981 Wakabayashi et al. ............. 548/264

FOREIGN PATENT DOCUMENTS 874406 2/1979 Belgium .

OTHER PUBLICATIONS

Shigematsu et al., Chem. Abstracts, vol. 88, Abstract No. 6891e (1978).

Primary Examiner—Alton D. Hollins

[57] ABSTRACT

A series of condensed heterocycles, more particularly condensates of triazolones with pyrazolones, which exhibit antibotrytical activity, are disclosed. A process for producing the new heterocycles, which are pyrozolo-triazol-triones, by reacting carbethoxy pyrazolones with isocyanates, in the presence of tertiary amines, is also disclosed.

8 Claims, No Drawings

ANTIBOTRYTICAL PYRAZOLO-TRIAZOL-TRIONES

THE PRIOR ART

Belgian Pat. No. 874,406 describes fungicidally active N-aryl-1,3-oxyazolidin-2,4-diones substituted in position 5 with a carboxylic group, and having the general formula:

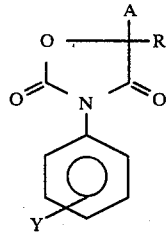

Fungicidally active derivatives of 4-(3'-5'-dichlorophenyl)-1,2,4-triazolidindione are disclosed in Japanese Pat. No. 77/83562.

THE PRESENT INVENTION

An object of the present invention is to provide pyrazolo[1,2-a]-[1,2,4]-triazol-1,3,5(2H)-triones which are antibotrytical and specifically active against *Botrytis cynerea*.

Another object is to provide a process for producing the pyrazolo-triazol-triones.

These and other objects are achieved by this invention in accordance with which pyrazolo-[1,2,a]-[1,2,4]-triazol-1,3,5-triones endowed with excellent antibotrytical activity and having the general formula

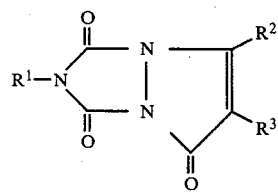

in which $R^1$ is a $C_1$–$C_5$ alkyl, phenyl optionally substituted by alkyl, trihaloalkyl, alkoxy, $NO_2$ or halogen, and particularly the group 3,5-dihalophenyl; and $R^2$ and $R^3$ are obtained by reacting a carbethoxy pyrazolone of the general formula

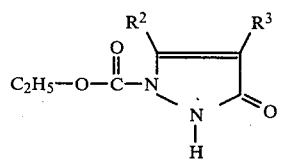

in which $R^2$ and $R^3$ have the same meaning as in formula (I), with an isocyanate of formula

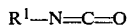

in an inert solvent, preferably an aromatic hydrocarbon such as benzene, in the presence of an equimolar amount of a tertiary amine, at a temperature comprised between room and the boiling temperature.

The reaction proceeds as follows:

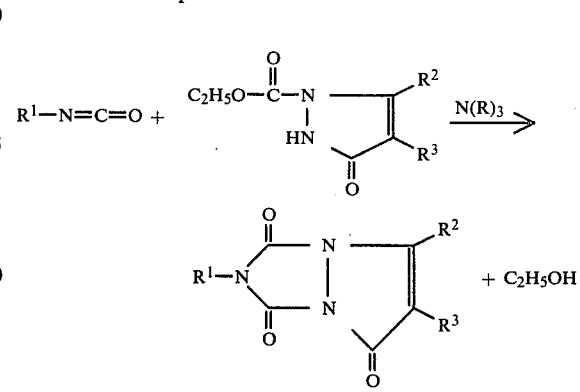

Under these conditions, when the solvent is benzene, the pyrazolo-triazol-trione-derivative may precipitate as the reaction proceeds.

Since the isocyanate may react with the ethanol freed by the reaction, to yield the corresponding $R^1$—NH—$COO_2H_5$ carbamate, it is possible to have the above-indicated reaction occur in two stages, by first condensing an equimolar quantity of isocyanate with the carbethoxy pyrazolone at room temperature, in the presence of catalytic quantities of tertiary amine, and then, once the reaction has been completed, the remaining tertiary amine in order to attain the equimolar quantity necessary for obtaining the triazolidinic ring closing, according to the following reaction scheme:

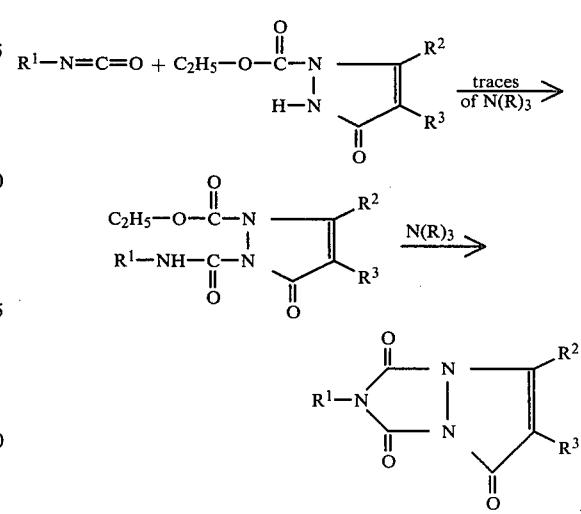

The compounds shown in Table I, among others, were thus prepared, the starting 2-ethoxycarbonyl-3-pyrazolidin-5-one being obtained by reacting the substituted pyrazolone with ethyl chloroformate.

TABLE I

Compounds of general formula R¹—N 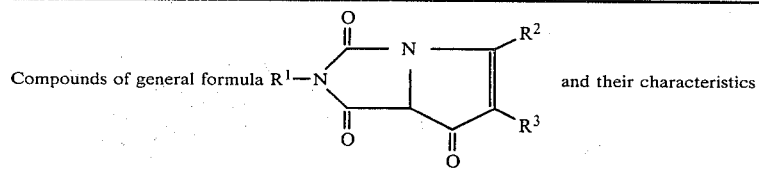 and their characteristics

| Compound No. | DENOMINATION | SUBSTITUENTS R¹ | R² | R³ | M.P. (°C.) | CRYSTAL. SOLVENT | FORMULA |
|---|---|---|---|---|---|---|---|
| 1 | Pyrazolo[1,2-a][1,2,4]triazol-1,3,5-trione-2-phenyl-7-methyl | $C_6H_5$ | $CH_3$ | H | 164–166 | ethanol | $C_{12}H_9N_3O_3$ |
| 2 | Pyrazolo[1,2-a][1,2,4]triazol-1,3,5-trione-2(4-chlorophenyl)-7-methyl | $4ClC_6H_4$ | $CH_3$ | H | 216–218 | ethanol | $C_{12}H_8ClN_3O_3$ |
| 3 | Pyrazolo[1,2-a][1,2,4]triazol-1,3,5-trione-2(3-chlorophenyl)-7-methyl | $3Cl-C_6H_4$ | $CH_3$ | H | 164–165 | ethanol | $C_{12}H_8ClN_3O_3$ |
| 4 | Pyrazolo[1,2-a][1,2,4]triazol-1,3,5-trione-2(3,4-dichlorophenyl)-7-methyl | $3,4Cl_2C_6H_3$ | $CH_3$ | H | 249–251 | ethanol | $C_{12}H_7Cl_2N_3O_3$ |
| 5 | Pyrazolo[1,2-a][1,2,4]triazol-1,3,5-trione-2(2',5',dichlorophenyl)-7-methyl | $3,5Cl_2C_6H_3$ | $CH_3$ | H | 200–202 | ethanol | $C_{12}H_7Cl_2N_3O_3$ |
| 6 | Pyrazolo[1,2-a][1,2,4]triazol-1,3,5-trione-2(4'-fluorophenyl)7-methyl | $4FC_6H_4$ | $CH_3$ | H | 197–198 | ethanol | $C_{12}H_8FN_3O_3$ |
| 7 | Pyrazolo[1,2-a][1,2,4]triazol-1,3,5-trione-2'(4'-tolyl)-7-methyl | $4CH_3C_6H_4$ | $CH_3$ | H | 164–166 | ethanol | $C_{13}H_{11}N_3O_3$ |
| 8 | Pyrazolo[1,2-a][1,2,4]triazol-1,3,5-trione-2(3',5',-dimethylphenyl)-7-methyl | $3,5(CH_3)_2C_6H_3$ | $CH_3$ | H | 203–205 | ethanol | $C_{14}H_{13}N_3O_3$ |
| 9 | Pyrazolo[1,2-a][1,2,4]triazol-1,3,5-trione-2(3',5',-dimethoxyphenyl)-7-methyl | $3,5(CH_3O)_2C_6H_3$ | $CH_3$ | H | 220–221 | benzene | $C_{14}H_{13}N_3O_3$ |
| 10 | Pyrazolo[1,2-a][1,2,4]triazol-1,3,5-trione-2(4-nitrophenyl)-7-methyl | $4NO_2-C_6H_4$ | $CH_3$ | H | 226–228 | ethanol | $C_{12}H_8N_4O_5$ |
| 11 | Pyrazolo[1,2-a][1,2,4]triazol-1,3,5-trione-2(3',5'-bis-trifluoromethyl-phenyl)-7-methyl | $3,5(CF_3)_2C_6H_3$ | $CH_3$ | H | 146–148 | ethanol | $C_{14}H_7F_6N_3O_3$ |
| 12 | Pyrazolo[1,2-a][1,2,4]triazol-1,3,5-trione-2,7-dimethyl | $CH_3$ | $CH_3$ | H | 116–117 | ethanol | $C_7H_7N_3O_3$ |
| 13 | Pyrazolo[1,2-a][1,2,4]triazol-1,3,5-trione-2(3',5'-dichlorophenyl)-7n . propyl | $nC_3H_7$ | $nC_3H_7$ | H | 156–158 | ethanol | $C_{14}H_{11}Cl_2N_3O_3$ |
| 14 | Pyrazolo[1,2-a][1,2,4]triazol-1,3,5-trione-2(3',5'-dichlorophenyl)-6-ethyl-7-methyl | $3,5Cl_2C_6H_3$ | $CH_3$ | $C_2H_5$ | 144–145 | ethanol | $C_{14}H_{11}Cl_2N_3O_3$ |

| Compound No. | PERCENTUAL ANALYSIS | | | | | | | |
|---|---|---|---|---|---|---|---|---|
| | % C | | % H | | % N | | % Cl | |
| | Calc. | Found | Calc. | Found | Calc. | Found | Calc. | Found |
| 1 | 59.10 | 59.13 | 3.70 | 3.50 | 17.25 | 17.30 | | |
| 2 | 51.91 | 51.84 | 2.90 | 2.79 | 15.13 | 15.14 | 12.77 | 12.83 |
| 3 | 51.91 | 51.57 | 2.90 | 2.71 | 15.13 | 15.20 | 12.77 | 12.67 |
| 4 | 46.18 | 46.29 | 2.26 | 2.14 | 13.46 | 13.33 | 22.72 | 22.79 |
| 5 | 46.18 | 46.30 | 2.26 | 2.13 | 13.46 | 13.75 | 22.72 | 22.51 |
| 6 | 55.0 | 54.85 | 3.06 | 3.05 | 15.55 | 15.75 | | |
| 7 | 60.70 | 59.95 | 4.31 | 4.53 | 16.33 | 16.21 | | |
| 8 | 61.99 | 61.42 | 4.83 | 4.87 | 15.49 | 15.58 | | |
| 9 | 55.45 | 55.56 | 4.32 | 4.16 | 13.85 | 13.71 | | |
| 10 | 50.01 | 50.37 | 2.80 | 2.89 | 19.44 | 19.14 | | |
| 11 | | | | | 11.09 | 11.18 | | |
| 12 | 46.41 | 46.83 | 3.89 | 3.85 | 23.20 | 23.43 | | |
| 13 | 49.43 | 49.19 | 3.26 | 3.22 | 12.35 | 12.36 | 20.85 | 21.02 |
| 14 | 49.43 | 49.22 | 3.26 | 3.02 | 12.35 | 12.20 | 20.85 | 21.17 |

The compounds of this invention act "in vitro" as well as "in vivo" to inhibit the growth of *Botrytis cynerea*.

The inhibiting action "in vitro" at a concentration of 100 p.p.m. is recorded in the following Table II.

TABLE II

Fungicide activity "in vitro" against *Botrytis Cynerea*, expressed as inhibition of growth after 96h at 22° C.

| Compound No. | Formula | Index of activity at 100 ppm* |
|---|---|---|
| 1 | | 3 |

TABLE II-continued

Fungicide activity "in vitro" against *Botrytis Cynerea*, expressed as inhibition of growth after 96h at 22° C.

| Compound No. | Formula | Index of activity at 100 ppm* |
|---|---|---|
| 2 | Cl-C₆H₄-N(CO)₂N-N=C(CH₃)-CH=CO (structure) | 2 |
| 3 | Cl-C₆H₄-N(CO)₂N-N=C(CH₃)-CH=CO (structure) | 3 |
| 4 | 3,4-Cl₂-C₆H₃-N(CO)₂N-N=C(CH₃)-CH=CO (structure) | 2 |
| 5 | 3,5-Cl₂-C₆H₃-N(CO)₂N-N=C(CH₃)-CH=CO (structure) | 3 |
| 6 | F-C₆H₄-N(CO)₂N-N=C(CH₃)-CH=CO (structure) | 2 |
| 7 | CH₃-C₆H₄-N(CO)₂N-N=C(CH₃)-CH=CO (structure) | 1 |
| 8 | 3,5-(CH₃)₂-C₆H₃-N(CO)₂N-N=C(CH₃)-CH=CO (structure) | 3 |
| 13 | 3,5-Cl₂-C₆H₃-N(CO)₂N-N=C(nC₃H₇)-CH=CO (structure) | 3 |

*Inhibition between 0 and 25% = 0; between 26 and 50% = 1; between 51 and 75% = 2; greater than 76% = 3.

The pyrazolo-triazol-triones may be formulated according to known techniques, in the form of powders, wettable powders, aqueous emulsions or suspension, solutions in organic solvents, possibly with the aid of surfactants, dispersants or diluents.

The following examples are given to illustrate the invention in more detail, and are not intended to be limiting.

EXAMPLE 1

Pyrazolo[1,2-a][1,2,4]-triazol-1,3,5-trione-2-phenyl-7-methyl (Compound No. 1)

A mixture of 5.1 g of 2-carboxyethyl-3-methyl-3-pyrazolin-5-one, 3.6 g of phenylisocyanate and 3 g of triethylamine in 80 ml of anhydrous benzene was heated for 7 hours at 50° C.

Thereupon, the solvent was removed by evaporation at reduced pressure and the residue was diluted with 150 ml of chloroform. The chloroform solution was then washed twice with 30 ml of water. This latter was recovered as such by acidification of the combined aqueous extracts with diluted hydrochloric acid and by successive filtering of the solid that separated (2.4 g).

From the chloroform solution, after anhydrification on sodium sulphate, and by evaporation of the solvent at reduced pressure, there was obtained an oily residue which was repeatedly diluted with petroleum ether. The low-melting solid thus obtained consisted of a mixture of ethyl phenylcarbamate and compound No. 1.

By crystallization from ethanol, there were obtained 1.7 grams of compound No. 1 with a melting point of 164°–166° C.

The IR analysis resulted: (in nujol) $\nu_{max.}=1820, 1810, 1740, 1695, 1585$ cm$^{-1}$;

The NMR analysis: $(CDCl_3)\delta=7.4$ (S, 5H, aromatics); 5.5 (S, 1H, unsaturated CH); 2.5

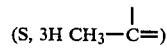

(S, 3H CH₃—C=)

Percent analyses: for $C_{12}H_9N_3O_3$

Calculated %: C=59.10; H=3.70; N=17.25; Found %: C=59.13; H=3.50; N=17.30.

EXAMPLE 2

Pyrazolo[1,2-a]-[1,2,4]-triazol-1,3,5-trione-2-(3′,5′-dichlorophenyl)-7-methyl (Compound No. 5)

(a) Into a suspension consisting of 5.1 g of 2-carboxyethyl-3-methyl-3-pyrazolin-5-one in 50 ml of anhydrous benzene, was dripped, at room temperature, a solution of 11.3 g of 3,5-dichlorophenylisocyanate in 50 ml of anhydrous benzene and 3 g of triethylamine.

The solution, after the addition of triethylamine, became clear and was maintained at 40°–45° C. for 4 hours. By cooling down to room temperature, there was obtained a solid which was then filtered and washed with benzene.

Thereby were obtained 6 grams of a raw product having a melting point of 195°–198° C., and which, crystallized from ethanol, yielded 5.4 grams of compound No. 5 in the form of crystals having a melting point of between 200° and 202° C.

IR: (nujol) $\nu_{max}=1815, 1755, 1720, 1585, 1570$ cm$^{-1}$
NMR: $(CDCl_3)$ $\delta=7.5$ (m, 3H, Aromatics; 5.6 (S, 1H, unsaturated CH); 2.6

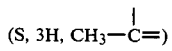

(S, 3H, CH₃—C=)

Mass: $m/e=311$ (M+), 187 (M+-

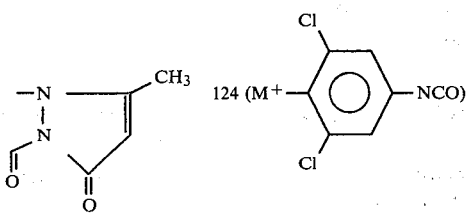 124 (M+ 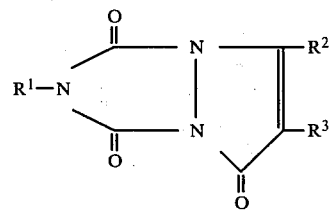

Analysis: for $C_{12}H_7Cl_2N_3O_3$

Calculated %: C=46.18; H=2.26; N=13.46; Cl=22.72; Found %: C=46.30; H=2.13; N=13.75; Cl=22.51.

(b) Reaction conducted on the above indicated quantities, keeping the solution on reflux for 2.30 hours. The raw product, amounting to 5.6 g, with m.p.=195°–198° C., by crystallization from ethanol, yielded 5 g of a product with a m.p. of 202° C.

(c) To a suspension of 3.4 g of 2-carboxyethyl-3-methyl-3-pyrazolin-5-one in 40 ml of anhydrous benzene, under stirring and at room temperature, were added a solution of 3.8 g of 3,5-dichlorophenylisocyanate in 40 ml of anhydrous benzene and 2 drops of triethylamine.

After 10 minutes, there separated a white, flaky precipitate, presumably 1(3',5'-dichloro-phenylcarbamoyl)-2-carboxyethyl-3-pyrazolin-5-one. To the solution thus obtained were added 2 g of triethylamine. The solution rapidly became clear and was then maintained at 45° C. for 3 hours.

The benzene was then evaporated at reduced pressure and the residue was diluted with 150 ml of chloroform. The solution was washed with water, then anhydrified on sodium sulphate and, finally, was evaporated at reduced pressure.

The raw residue thus obtained, after having been crystallized twice from ethanol, yielded 2.3 g of compound No. 5 that had a melting point=194° C., while its I.R. spectrum proved identical with that of the sample obtained according to process (a).

EXAMPLE 3

Pyrazolo-[1,2-a][1,2,4]-triazol-1,3,5-trione-2,7-dimethyl. (Compound No. 12)

Into a suspension consisting of 6.8 g of 2-carboxyethyl-3-methyl-3-pyrazolin-5-one in 100 ml of anhydrous benzene were dripped 4.6 g of methylisocyanate and 4 g of triethylamine. The benzene solution became clear and was then kept at a temperature of between 45° and 50° C. for 6 hours.

Thereafter, the solvent was removed at reduced pressure, the residue was diluted with 100 ml of chloroform and this latter was washed with 15 ml of water, and then anhydrified on sodium sulphate.

By evaporation of the solvent at reduced pressure, there were obtained 8 g of a thick oil which, repeatedly diluted with petroleum ether, when cold, solidified. By crystallization from ethanol, there were obtained 4.6 g of a white, crystalline solid with a melting point of 115°–117° C. (compound No. 12).

IR analysis: (nujol) $\nu_{max.}$=1815, 1740, 1675, 1580 cm$^{-1}$

NMR analysis: (CDCl$_3$) $\delta$=5.5 (S, 1H, unsaturated CH); 3.13 (S, 3H, N—CH$_3$); 2.5 (S, 3H, CH$_3$—C=)

Percent analysis for $C_7H_7N_3O_3$

Calculated %: C=46.41; H=3.89; N=23.20; Found %: C=46.53; H=3.85; N=23.43.

What is claimed is:

1. Pyrazolo-[1,2-a]-[1,2,4]-triazol-1,3,5-[2H]-triones having the general formula $$\text{structure with } R^1-N, R^2, R^3$$

in which
R$^1$ is lower alkyl, phenyl, phenyl substituted by lower alkyl, lower alkoxyl, trihalomethyl, NO$_2$ or halogen; and
R$^2$ and R$^3$, the same or different, are H or lower alkyl.

2. Pyrazolo-[1,2,a]-[1,2,4]-triazol-1,3,5-[2H]-triones according to claim 1, in which R$^1$ is dihalophenyl.

3. Pyrazolo-[1,2,a]-[1,2,4]-triazol-1,3,5-trione-2-(3',5'-dichlorophenyl)-7-methyl.

4. Pyrazolo-[1,2,a]-[1,2,4]-triazol-1,3,5-trione-2-(3'-chlorophenyl)-7-methyl.

5. Pyrazolo-[1,2,a]-[1,2,4]-triazol-1,3,5-trione-2-(3'-5'-dimethylphenyl)-7-methyl.

6. Pyrazolo-[1,2,a]-[1,2,4]-triazol-1,3,5-trione-2-(3',5'-dichlorophenyl)-7-n-propyl.

7. Method for preventing infections by Botrytis cinerea on useful plants, said method consisting in sprinkling the plants with the compounds of claim 1, either as such or in the form of compositions containing said compounds, in quantities of at least 0.75% upward.

8. Compositions suited for fighting infections by Botrytis cinerea on useful plants, said compositions containing an antibotrytical amount of at least one compound according to claim 1, and being in the form of a powder, suspension, emulsion or solution.

* * * * *